US011618723B2

(12) United States Patent
Xu et al.

(10) Patent No.: US 11,618,723 B2
(45) Date of Patent: Apr. 4, 2023

(54) INTEGRATED PROCESS FOR OPTIMUM PRODUCTION OF PARA-XYLENE

(71) Applicant: Saudi Arabian Oil Company, Dhahran (SA)

(72) Inventors: Qi Xu, Dhahran (SA); Zhonglin Zhang, Dhahran (SA); Raed Abudawoud, Khobar (SA)

(73) Assignee: Saudi Arabian Oil Company, Dhahran (SA)

( * ) Notice: Subject to any disclaimer, the term of this patent is extended or adjusted under 35 U.S.C. 154(b) by 220 days.

(21) Appl. No.: 17/143,109

(22) Filed: Jan. 6, 2021

(65) Prior Publication Data

US 2021/0122689 A1 Apr. 29, 2021

Related U.S. Application Data

(60) Division of application No. 16/592,158, filed on Oct. 3, 2019, now Pat. No. 10,894,755, which is a (Continued)

(51) Int. Cl.
*C07C 4/18* (2006.01)
*C07C 5/27* (2006.01)
(Continued)

(52) U.S. Cl.
CPC ............... *C07C 15/08* (2013.01); *B01D 3/14* (2013.01); *B01J 19/1825* (2013.01); *C07C 4/12* (2013.01);
(Continued)

(58) Field of Classification Search
CPC .... C07C 4/18; C07C 6/06; C07C 5/27; C07C 5/277; C07C 5/2732; C07C 6/04; C07C 4/14
See application file for complete search history.

(56) References Cited

U.S. PATENT DOCUMENTS 4,013,734 A 3/1977 Kim
4,127,471 A 11/1978 Suggitt et al.
(Continued)

FOREIGN PATENT DOCUMENTS

CN 105622306 A 6/2016
EP 0816311 A1 1/1998
(Continued)

OTHER PUBLICATIONS

Alario, et al., "Para-xylene Manufacturing: Catalytic Reactions and Processes," 3 Catalytic Science Series: Zeolites for Cleaner Technologies (2002), 189-207.
(Continued)

*Primary Examiner* — Youngsul Jeong
(74) *Attorney, Agent, or Firm* — Bracewell LLP; Constance G. Rhebergen; Eleanor L. Tyson

(57) ABSTRACT

A method of producing p-xylene comprising the steps of separating the reformate feed in the reformate splitter to produce a benzene stream, a combined heavy stream, a xylene stream, and a toluene stream, converting the C9+ aromatic hydrocarbons in the presence of a dealkylation catalyst in the dealkylation reactor to produce a dealkylation effluent, separating the dealkylation effluent in the dealkylation splitter to produce a C9 stream and a C10+ stream, reacting the C9 stream, the toluene stream, the benzene stream, and the hydrogen stream in the presence of a transalkylation catalyst in the transalkylation reactor to produce a transalkylation effluent, separating the p-xylenes from the xylene stream in the p-xylene separation unit to produce a p-xylene product and a p-xylene depleted stream, converting the m-xylene and o-xylene in the p-xylene depleted stream in the isomerization unit to produce an isomerization effluent.

6 Claims, 7 Drawing Sheets

Related U.S. Application Data continuation-in-part of application No. 16/160,393, filed on Oct. 15, 2018, now Pat. No. 10,696,609.

(51) Int. Cl.

| | |
|---|---|
| C07C 6/06 | (2006.01) |
| C07C 15/08 | (2006.01) |
| B01D 3/14 | (2006.01) |
| B01J 19/18 | (2006.01) |
| C07C 4/12 | (2006.01) |

(52) U.S. Cl.
CPC .. *B01D 2256/24* (2013.01); *B01D 2257/7027* (2013.01); *B01J 2203/06* (2013.01)

(56) References Cited

U.S. PATENT DOCUMENTS

| | | | |
|---|---|---|---|
| 4,172,813 | A | 10/1979 | Bertolacini et al. |
| 4,310,715 | A | 1/1982 | Dorawala et al. |
| 5,004,854 | A | 4/1991 | Yan |
| 5,030,787 | A | 7/1991 | Absil et al. |
| 5,763,720 | A | 6/1998 | Buchanan et al. |
| 5,847,256 | A | 12/1998 | Ichioka et al. |
| 5,866,741 | A | 2/1999 | Wu et al. |
| 5,942,651 | A | 8/1999 | Beech, Jr. et al. |
| 5,952,536 | A | 9/1999 | Nacamuli et al. |
| 6,024,422 | A | 2/2000 | Drennen et al. |
| 6,096,938 | A | 8/2000 | Ghosh |
| 6,204,422 | B1 | 3/2001 | Tsutsui et al. |
| 6,359,184 | B1 | 3/2002 | Kato et al. |
| 6,706,937 | B2 | 3/2004 | Xiao et al. |
| 7,288,687 | B1 | 10/2007 | Frey et al. |
| 7,544,849 | B2 | 6/2009 | Boldingh et al. |
| 7,553,998 | B2 | 6/2009 | Bresler |
| 7,563,358 | B2 | 7/2009 | Stavens et al. |
| 7,663,010 | B2 * | 2/2010 | Levin .................. B01J 29/7469 585/475 |
| 7,727,490 | B2 | 6/2010 | Zhou |
| 8,071,828 | B2 | 12/2011 | Cao et al. |
| 8,084,657 | B2 * | 12/2011 | Kong ..................... C10G 65/00 585/812 |
| 8,183,424 | B2 | 5/2012 | Levin et al. |
| 8,198,502 | B2 | 6/2012 | Bresler et al. |
| 8,431,758 | B2 | 4/2013 | Frey et al. |
| 8,822,747 | B2 | 9/2014 | Corradi et al. |
| 9,000,247 | B2 | 4/2015 | Abudawoud |
| 9,249,068 | B2 | 2/2016 | Tinger et al. |
| 9,295,970 | B1 | 3/2016 | Tinger et al. |
| 9,302,953 | B2 | 4/2016 | Molinier et al. |
| 9,469,579 | B2 | 10/2016 | Molinier et al. |
| 10,035,742 | B1 | 7/2018 | Xu et al. |
| 2005/0197518 | A1 | 9/2005 | Miller et al. |
| 2006/0178544 | A1 | 8/2006 | Murray et al. |
| 2007/0203376 | A1 | 8/2007 | Negiz et al. |
| 2008/0021253 | A1 | 1/2008 | Corma Canos et al. |
| 2009/0112034 | A1 | 4/2009 | Levin |
| 2009/0234170 | A1 | 9/2009 | Lee et al. |
| 2012/0024755 | A1 | 2/2012 | Beech, Jr. et al. |
| 2012/0083638 | A1 | 4/2012 | Boldingh et al. |
| 2012/0271071 | A1 | 10/2012 | Haizmann et al. |
| 2012/0271084 | A1 | 10/2012 | Haizmann et al. |
| 2013/0165719 | A1 | 6/2013 | Negiz et al. |
| 2013/0261365 | A1 | 10/2013 | Wang et al. |
| 2014/0100402 | A1 | 4/2014 | Gawlik et al. |
| 2015/0094508 | A1 | 4/2015 | Corradi et al. |
| 2015/0166435 | A1 | 6/2015 | Serban et al. |
| 2015/0376086 | A1 | 12/2015 | Tinger et al. |
| 2016/0046544 | A1 | 2/2016 | Molinier et al. |
| 2016/0101405 | A1 | 4/2016 | Tinger et al. |
| 2016/0185686 | A1 | 6/2016 | Molinier et al. |
| 2016/0311731 | A1 | 10/2016 | Amelse |
| 2017/0152198 | A1 | 6/2017 | Colling |
| 2017/0349508 | A1 | 12/2017 | Montalbano et al. |
| 2021/0122689 | A1 | 4/2021 | Xu et al. |

FOREIGN PATENT DOCUMENTS

| | | | |
|---|---|---|---|
| WO | 0010944 | A1 | 3/2000 |
| WO | 2004056945 | A1 | 7/2004 |
| WO | 2007137017 | A1 | 11/2007 |
| WO | 2008094255 | A1 | 8/2008 |
| WO | 2012006039 | A2 | 1/2012 |
| WO | 2013158956 | A1 | 10/2013 |
| WO | WO-2013158956 | A1 * | 10/2013 ............. B01J 8/08 |

OTHER PUBLICATIONS

Arribas, "The Influence of Zeolite Acidity for the Coupled Hydrogenation and Ring Opening of 1-Methylnaphthalene an Pt/USY Catalysts"; Elsevier, Applied Catalysis A: General 230 (2000) 203-217; 15 pgs.

Commissaris, Scott E.; "UOP Parex Process", Handbook of Petroleum Refining Processes Third Edition, 2004, Chapter 2.6, pp. 2.47-2.53.

Eliche-Quesada, et al.; "Effects of Preparation Method and Sulfur Poisoning on The Hydrogenation and Ring Opening of Tetralin on NiW/Zirconium-Doped Mesoporous Silica Catalysts"; Elsevier, Journal of Catalysis 220 (2003) 457-467; 11 pgs.

International Search Report and the Written Opinion for International Application No. PCT/US2013/037304 (SA5038/PCT) dated Jul. 4, 2013; pp. 1-9.

International Search Report and Written Opinion for International Application No. PCT/US2018/012129 (SA5565) International Filing Date Jan. 3, 2018; Report dated Apr. 24, 2018 (pp. 1-14).

International Search Report and Written Opinion for International Application No. PCT/US2018/032874 (SA5633) Report dated Jul. 5, 2018; 13 pgs.

International Search Report and Written Opinion for related PCT application PCT/US2019/056245 dated Mar. 3, 2020. (SA5965PCT).

Johnson, James A.; "Aromatics Complexes", Handbook of Petroleum Refining Processes Third Edition, 2004, Chapter 2.1, pp. 2.3-2.11.

Kim, et al.; "Novel Ni2P/Zeolite Catalysts for Naphthalene Hydrocracking to BTX"; Elsevier, Catalysis Communications 45 (2014) 133-138; 6 pgs.

Negiz, Antoine and Stoodt, Thomas J.; "UOP Tatoray Process", Handbook of Petroleum Refining Processes Third Edition, 2004, Chapter 2.7, pp. 2.55-2.63.

Silady, Patrick J.; "UOP Isomar Process", Handbook of Petroleum Refining Processes Third Edition, 2004, Chapter 2.5, pp. 2.39-2.46.

* cited by examiner

A2

INTEGRATED PROCESS FOR OPTIMUM PRODUCTION OF PARA-XYLENE

REFERENCE TO CROSS-RELATED APPLICATIONS

This application is divisional application of U.S. Non-Provisional patent application Ser. No. 16/592,158 filed on Oct. 3, 2019, which is a continuation-in-part application of U.S. Non-Provisional patent application Ser. No. 16/160,393 filed on Oct. 15, 2018 and issued as U.S. Pat. No. 10,696,609 on Jun. 30, 2020. For purposes of United States patent practice, this application incorporates the contents of both Non-Provisional Application by reference in their entirety.

TECHNICAL FIELD

Disclosed are methods and systems for production of xylenes. Specifically, disclosed are methods and systems for maximizing production of xylenes from reformate.

BACKGROUND

In a typical aromatics complex catalytic naphtha reformate is directed to benzene-toluene-xylene (BTX) separation steps and the remaining C9+ fraction can be separated into a C9 fraction and a C10+ fraction. The C10+ fraction can be rejected from the system.

The C9 fraction can be introduced to a transalkylation reactor to produce additional BTX. The extracted xylenes can be directed to a para-xylene separation step. The remaining xylene isomers can be sent to a stand-alone xylene isomerization reactor to re-establish the thermodynamic equilibrium of xylenes and form para-xylene in the process.

Benzene can be separated from the catalytic naphtha reformate via the extraction process. In addition, benzene can be produced in the toluene disproportionation reactor, through thermal dealkylation, or hydrodealkylation. The produced benzene is recovered from the process. In a typical process, the benzenes recovered or produced are not recycled within the process. Additional xylenes can be produced in the thermal dealkylation and hydrodealkylation.

SUMMARY

Disclosed are methods and systems for production of xylenes. Specifically, disclosed are methods and systems for maximizing production of xylenes from reformate.

In a first aspect, a method of producing para-xylene (p-xylene) is provided. The method includes the steps of introducing a reformate feed to reformate splitter, the reformate splitter configured to separate the reformate feed, the reformate feed includes aromatic hydrocarbons, where the aromatic hydrocarbons are selected from the group consisting of benzene, toluene, mixed xylenes, carbon-nine plus (C9+) aromatic hydrocarbons, and combinations of the same and separating the reformate feed in the reformate splitter to produce a light gases stream, a benzene stream, a combined heavy stream, a xylene stream, and a toluene stream, where the combined heavy stream includes C9+ aromatic hydrocarbons, and where the xylene stream includes mixed xylenes, where the mixed xylenes includes p-xylenes, and where the toluene stream includes toluene. The method further includes the steps of introducing the combined heavy stream to a dealkylation reactor, introducing a hydrogen feed to the dealkylation reactor, where the hydrogen feed includes hydrogen gas, where the dealkylation reactor is configured to the convert C9+ aromatic hydrocarbons to carbon-six (C6) to carbon-eight (C8) aromatic hydrocarbons, and converting the C9+ aromatic hydrocarbons and the hydrogen gas in the presence of a dealkylation catalyst in the dealkylation reactor to produce a dealkylation effluent, where the dealkylation reactor is at a dealkylation temperature, where the dealkylation reactor is at a dealkylation pressure, where the dealkylation effluent includes aromatic hydrocarbons such that an amount of C9+ aromatic hydrocarbons in the dealkylation effluent is less than the amount of C9+ aromatic hydrocarbons in the reformate feed. The method further includes the steps of introducing the dealkylation effluent to a dealkylation splitter, the dealkylation splitter configured to separate the dealkylation effluent, separating the dealkylation effluent in the dealkylation splitter to produce a C9 stream, a C10+ stream, and a light recycle stream, where the C10+ stream includes C10+ aromatic hydrocarbons, where the C9 stream includes C9 aromatic hydrocarbons, introducing the C9 stream and a hydrogen stream to a transalkylation reactor, the transalkylation reactor configured to convert C9 aromatic hydrocarbons through transalkylation reactions, where the hydrogen stream includes hydrogen gas, introducing the benzene stream to the transalkylation reactor, introducing the toluene stream as a toluene split stream to the transalkylation reactor, where a flow rate of the toluene split stream is operable to maintain a ratio of toluene to trimethylbenzene in the transalkylation reactor in the range of 0.3 to 3, and reacting the C9 stream, the toluene stream, the benzene stream, and the hydrogen stream in the presence of a transalkylation catalyst in the transalkylation reactor to produce a transalkylation effluent, where the transalkylation reactor is at a transalkylation temperature, where the transalkylation reactor is at a transalkylation pressure, where the transalkylation catalyst is operable to catalyze transalkylation reactions, where the transalkylation effluent includes C6 to C9+ aromatic hydrocarbons. The method further includes the steps of introducing the xylene stream to a p-xylene separation unit, the p-xylene separation unit configured to separate p-xylenes from the xylene stream, separating the p-xylenes from the xylene stream in the p-xylene separation unit to produce a p-xylene product and a p-xylene depleted stream, where the p-xylene product includes p-xylenes, where the p-xylene depleted stream includes m-xylene and o-xylene, introducing the p-xylene depleted stream to an isomerization unit, where the isomerization unit includes an isomerization catalyst, and converting the m-xylene and o-xylene in the p-xylene depleted stream in the isomerization unit to produce an isomerization effluent, where the isomerization unit is at an isomerization temperature, where the isomerization unit is at an isomerization pressure, where the isomerization effluent includes C8 aromatic hydrocarbons. The method further includes the step of introducing the light recycle stream, the isomerization effluent and the transalkylation effluent to the reformate splitter.

In certain aspects, the method further includes the steps of introducing a fraction of the toluene stream not in the toluene split stream to a toluene disproportionation reactor, where the toluene disproportionation reactor includes a disproportion catalyst, where the toluene disproportionation reactor is configured to support a toluene disproportionation reaction, reacting the fraction of the toluene stream in the toluene disproportionation reactor to produce a disproportionation effluent, where the disproportionation effluent includes C6 to C8 aromatic hydrocarbons, and introducing the disproportionation effluent to the reformate column. In certain aspects, the method further includes the step of separating a fraction of the C10+ stream in a purge stream. In certain aspects, the dealkylation temperature is between 200 deg C. and 550 deg C., further where the dealkylation pressure is between 5 bar and 50 bar, and further where a liquid hourly space velocity in the dealkylation reactor is between 1 hr-1 and 20 hr-1. In certain aspects, the transalkylation temperature is between 200 deg C. and 550 deg C., further where the transalkylation pressure is between 10 bar and 50 bar, further where a liquid hourly space velocity in the transalkylation reactor is between 0.2 hr-1 and 20 hr-1. In certain aspects, the isomerization temperature is between 200 deg C and 550 deg C, further where the isomerization pressure is between 5 bar and 50 bar, and further where a liquid hourly space velocity in the isomerization unit is between 1 hr-1 and 20 hr-1.

In a second aspect, a system for producing para-xylene (p-xylene) from a reformate feed is provided. The system includes a reformate splitter, the reformate splitter configured to separate the reformate feed, where the reformate feed includes aromatic hydrocarbons, where the aromatic hydrocarbons are selected from the group consisting of benzene, toluene, mixed xylenes, carbon-nine plus (C9+) aromatic hydrocarbons, and combinations of the same, where the reformate splitter produces a light gases stream, a combined heavy stream, a benzene stream, a xylene stream, and toluene stream, where the C9 aromatics stream includes C9 aromatic hydrocarbons, and where the xylene stream includes mixed xylenes, where the mixed xylenes includes p-xylenes, and where the mixed light aromatics stream includes toluene. The system further includes a dealkylation reactor fluidly connected to the reformate splitter, the dealkylation reactor configured to convert C9+ aromatic hydrocarbons to carbon-six (C6) to carbon-eight (C8) aromatic hydrocarbons in the presence of a dealkylation catalyst to produce a dealkylation effluent, where the dealkylation reactor is at a dealkylation temperature, where the dealkylation reactor is at a dealkylation pressure, where the dealkylation effluent includes aromatic hydrocarbons such that an amount of C9+ aromatic hydrocarbons in the dealkylation effluent is less than the amount of C9+ aromatic hydrocarbons in the reformate feed and a dealkylation splitter fluidly connected to the dealkylation reactor, the dealkylation splitter configured to separate the dealkylation effluent to produce a light recycle stream, C10+ aromatics stream, and C9 stream. The system further includes a transalkylation reactor fluidly connected to the dealkylation reactor and fluidly connected to the reformate splitter, the transalkylation reactor configured to convert toluene and C9 aromatic hydrocarbons in the presence of a transalkylation catalyst to produce a transalkylation effluent, where the transalkylation reactor is at a transalkylation temperature, where the transalkylation reactor is at a transalkylation pressure, where the toluene is supplied by a toluene split stream, where the toluene split stream is separated from the toluene stream, where the transalkylation catalyst is operable to catalyze transalkylation reactions, where the transalkylation effluent includes C6 to C9+ aromatic hydrocarbons, a p-xylene separation unit fluidly connected to a reformate splitter, the p-xylene separation unit configured to separate p-xylenes from the xylene stream to produce a p-xylene product and a p-xylene depleted stream, where the p-xylene product includes p-xylenes, where the p-xylene depleted stream includes m-xylene and o-xylene, and an isomerization unit fluidly connected to the p-xylene separation unit, where the isomerization unit is configured to convert the m-xylene and o-xylene in the p-xylene depleted stream to produce an isomerization effluent, where the isomerization unit is at an isomerization temperature, where the isomerization unit is at an isomerization pressure, where the isomerization effluent includes C8 aromatic hydrocarbons.

In certain aspects, a flow rate of the toluene split stream is operable to maintain a ratio of toluene to trimethylbenzene in the transalkylation reactor in a range of 0.3 to 3. In certain aspects, the system further includes a toluene disproportionation reactor fluidly connected to the reformate splitter, the toluene disproportionation reactor configured to convert a fraction of the toluene from the toluene stream to produce a disproportionation effluent, where the disproportionation effluent includes C6 to C8 aromatic hydrocarbons.

BRIEF DESCRIPTION OF THE DRAWINGS

These and other features, aspects, and advantages of the scope will become better understood with regard to the following descriptions, claims, and accompanying drawings. It is to be noted, however, that the drawings illustrate only several embodiments and are therefore not to be considered limiting of the scope as it can admit to other equally effective embodiments.

Figure 1:
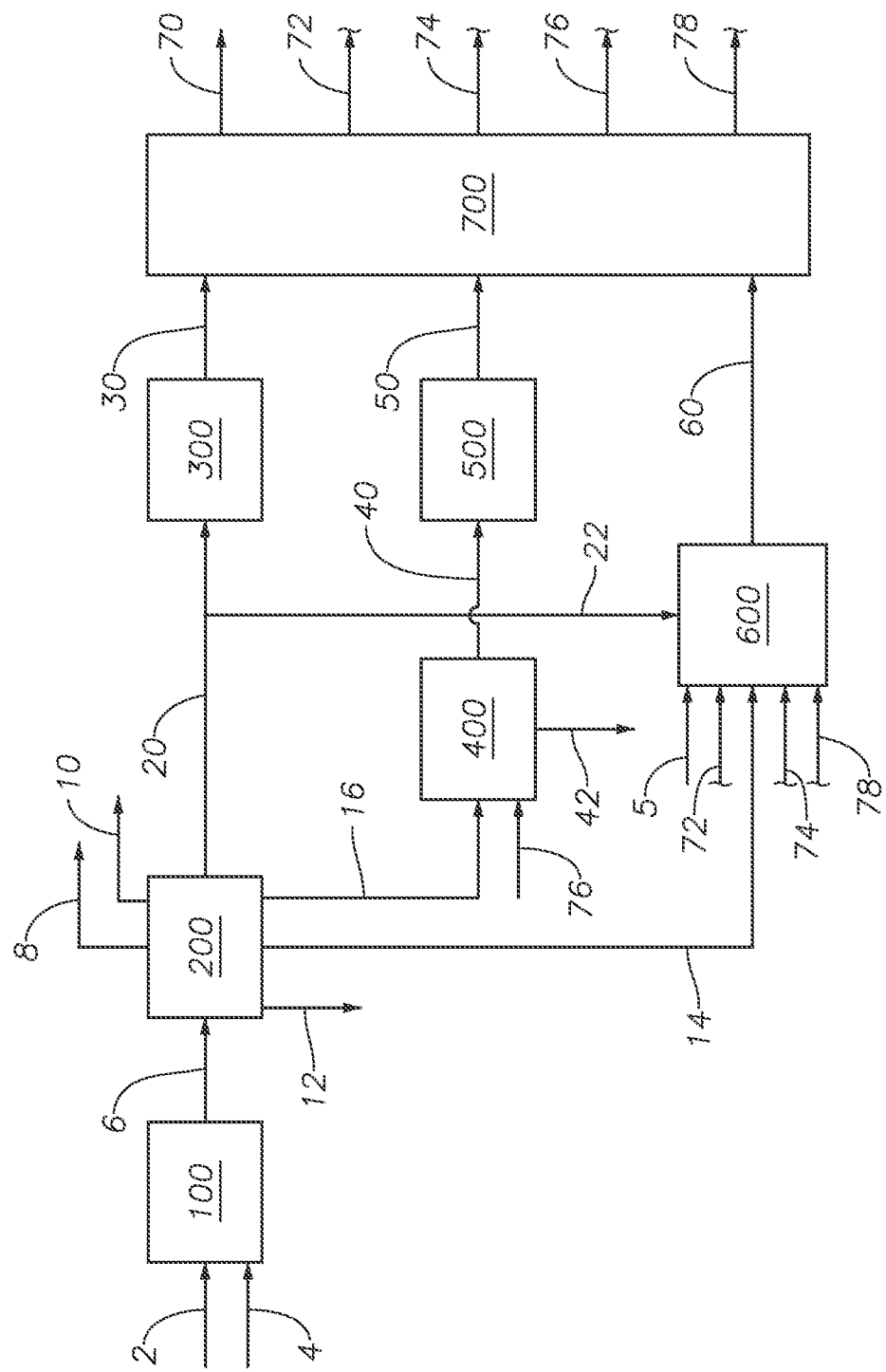
FIG. 1 provides a process diagram of an embodiment of the process.

In the accompanying Figures, similar components or features, or both, may have a similar reference label.

DETAILED DESCRIPTION

While the scope of the apparatus and method will be described with several embodiments, it is understood that one of ordinary skill in the relevant art will appreciate that many examples, variations and alterations to the apparatus and methods described here are within the scope and spirit of the embodiments.

Accordingly, the embodiments described are set forth without any loss of generality, and without imposing limitations, on the embodiments. Those of skill in the art understand that the scope includes all possible combinations and uses of particular features described in the specification.

Described here are processes and systems of a system to maximize production of mixed xylenes. A reformate is introduced to a dealkylation reactor. The dealkylation effluent from the dealkylation reactor is separated into the separate components in a reformate splitter. The mixed xylene stream is then separated to produce a p-xylene product stream. The p-xylene depleted stream is introduced to an isomerization unit to produce a mixed xylene stream and the mixed xylene stream is then introduced to a splitter column. The C9 aromatic hydrocarbons and toluene are introduced to a transalkylation reactor along with a benzene recycle, toluene recycle, and C9+ aromatic recycle from the splitter column. The transalkylation effluent is introduced to the splitter column where the effluent is separated into it components, thus producing the benzene recycle, the toluene recycle, and the C9+ aromatic hydrocarbons. The mixed xylenes separated from transalkylation effluent in the splitter column are recycled to the p-xylene separation.

The use of a dealkylation reactor can reduce the flow rate of heavy reformate going to the transalkylation reactor due to the conversion of methylethylbenzene to toluene in the dealkylation reactor. Advantageously, the use of a dealkylation reactor increases the production of mixed xylenes due to an increase in the conversion of C10+ aromatic hydrocarbons in the dealkylation reactor and a reduced amount or absence of C10+ aromatic hydrocarbons in the transalkylation reactor. Advantageously, the process to maximize the production of xylenes utilizes the entire reformate stream to produce valuable aromatics, by introducing the entire reformate stream to the dealkylation reactor before separating the stream to reject the C10+ fraction. In at least one embodiment, the C10+ aromatic hydrocarbons in the dealkylation reactor effluent can be inert and therefore do not contribute to the production of xylenes. Examples of inert C10+ aromatic hydrocarbons in the dealkylation reactor effluent include methyl-naphthalene (a C11 aromatic) and diethylbenzene (a C10 aromatic). Such inert C10+ aromatic hydrocarbons can cause deactivation of the catalyst in the transalkylation reactor and effectively lower the efficiency of transalkylation catalyst by diluting the feed. Advantageously, the use of the reformate splitter and the splitter column to separate the streams into component parts enhances the ability to process the components and increase the production of mixed xylenes as compared to broader cut separations. Advantageously the combination of the reformate splitter and the splitter column contributes to the increased production of mixed xylenes due to the ability to direct and recycle the use of each component stream. Advantageously, the combination of a dealkylation reactor and a separate transalkylation reactor increases the overall production of xylenes as compared to a one-reactor system that contains both a dealkylation catalyst and a transalkylation catalyst or a single catalyst capable of both dealkylation and transalkylation reactions. Advantageously, the use of separate units to perform disproportionation reactions, isomerization reactions, and dealkylation reactions, can allow each unit to be designed for a specific feed and specific catalyst and can therefore be optimized to maximize production of the target component.

As used throughout, a reference to "C" and a number or "carbon-number" refers to the number of carbon atoms in a hydrocarbon. For example, C1 refers to a hydrocarbon with one carbon atom and C6 refers to a hydrocarbon with six carbon atoms.

As used throughout, "C9 aromatic hydrocarbons" refers to aromatic hydrocarbons with nine carbon atoms. Examples of C9 aromatic hydrocarbons include methylethylbenzene, trimethylbenzene, propylbenzene, and combinations of the same.

As used throughout, "trimethylbenzene" or "TMB" refers to and includes each of the isomers of trimethylbenzene: hemellitene, pseudocumene, and mesitylene.

As used throughout, "C10+ aromatic hydrocarbons" refers to aromatic hydrocarbons with ten carbon atoms and aromatic hydrocarbons with more than ten carbon atoms, such as an aromatic hydrocarbon with eleven carbon atoms.

As used throughout, "C9+ aromatic hydrocarbons" refers to the group of C9 aromatic hydrocarbons and C10+ aromatic hydrocarbons.

As used throughout, "mixed xylenes" refers to one or more of para-xylene (p-xylene), meta-xylene (m-xylene), and ortho-xylene (o-xylene).

As used throughout, "dealkylation reaction" refers to a reaction that results in the removal of an alkyl group from one or more of the reactants. For example, a reaction to convert methylethylbenzene and hydrogen to ethane and p-xylene is a dealkylation reaction.

As used throughout, "transalkylation reaction" refers to a reaction that results in the transfer of an alkyl group from one or compound to another.

As used throughout, "isomerization reaction" refers to a reaction that results in the rearrangement of molecules to a different molecular structure, but the molecular formula remains the same. For example, a reaction to convert o-xylene to p-xylene or ethylbenzene to p-xylene is an isomerization reaction.

As used throughout, "light gases" refers to light hydrocarbons, hydrogen, air, and combinations of the same.

As used throughout, "light hydrocarbons" refers to alkanes, including methane, ethane, propane, butanes, pentanes, alkenes, and trace amounts of naphthenes, such as cyclopentane, cyclohexane, and combinations of the same.

Referring to FIG. 1 an embodiment of the process for increasing xylene production is provided.

Reformate feed 2 and hydrogen feed 4 are introduced to dealkylation reactor 100. Reformate feed 2 can include C6 to C12 one ring aromatic hydrocarbons. Reformate feed 2 can be sourced from a reformer unit. A reformer unit converts naphthas into aromatics-rich products and can use platinum-containing catalyst at high temperatures and hydrogen pressures to effect such conversions. The goal of a reformer unit is to increase the octane number of the reformer feed stream. The primary reactions in a reformer unit include dehydrogenation reactions, however, cracking reactions can also occur.

In at least one embodiment, reformate feed 2 can include benzene, toluene, mixed xylenes, C9 aromatic hydrocarbons, C10+ aromatic hydrocarbons, and combinations of the same. In at least one embodiment, the C10+ aromatic hydrocarbons can include C10 to C12 hydrocarbons. Reformate feed 2 can include between 65 percent by weight (wt %) and 80 wt %. Reformate feed 2 can further include paraffins and naphthenes in the range between 20 wt % and 35 wt %. The amount of aromatics and non-aromatics depends on the nature of the feed to the reformate unit and the severity of the conditions in the reactors of the reformate unit.

Hydrogen feed 4 can be any stream containing hydrogen gas. Hydrogen feed 4 can be a stream of pure hydrogen from a fresh hydrogen source. In at least one embodiment, hydrogen gas can be recovered from another part of the process and can be recycled as hydrogen feed 4 and introduced to dealkylation reactor 100. Hydrogen feed 4 can be from a hydrogen source in a refinery and can contain light hydrocarbons. The hydrogen gas in hydrogen feed 4 can ensure that the non-aromatics are not cracked to produce olefins. One of skill in the art understands that olefins are not formed in the presence of hydrogen, but paraffins can be. In an alternate embodiment for increasing xylene production, dealkylation reactor 100 can be in the absence of hydrogen, such as in a fluidized bed reactor, and olefins can be produced.

Dealkylation reactor 100 can be any type of reactor capable of containing and supporting a dealkylation reaction. Dealkylation reactor 100 can be a fixed bed reactor or a fluidized bed reactor. In embodiments with hydrogen feed 4, dealkylation reactor 100 can be a fixed bed reactor. In embodiments where dealkylation reactor 100 is in the absence of hydrogen, dealkylation reactor 100 can be a fluidized bed reactor. The dealkylation temperature in dealkylation reactor 100 can be between 200 degrees Celsius (deg C.) and 550 deg C. The dealkylation pressure in dealkylation reactor 100 can be between 5 bar (500 kilopascal (kPa)) and 50 bar (5000 kPa) and alternately between 10 bar (1000 kPa) and 50 bar (5000 kPa). The liquid hourly space velocity (LHSV) can be between 1 per hour ($hr^{-1}$) and 20 $hr^{-1}$ and alternately between 1 $hr^{-1}$ and 10 $hr^{-1}$. The volumetric flow ratio of hydrogen feed 4 to reformate feed 2 can be in the range of 0 to 8.

Dealkylation reactor 100 can include a dealkylation catalyst. The dealkylation catalyst can include any catalysts capable of catalyzing dealkylation reactions. Examples of dealkylation catalyst can include catalysts such as those described in U.S. Pat. No. 6,096,938 and those described in U.S. Pat. No. 9,000,247. The dealkylation catalyst can be selected to selectively convert one or more of the C9+ aromatic hydrocarbons over the others in dealkylation reactions. Dealkylation reactions can convert C9+ aromatic hydrocarbons to C6 to C8 aromatic hydrocarbons. Dealkylation reactions can convert C10+ aromatic hydrocarbons to C9 aromatic hydrocarbons. Reactions in dealkylation reactor 100 can remove methyl, ethyl, propyl, butyl and pentyl groups, and their isomers, attached to C10+ aromatic hydrocarbons. In at least one embodiment, a dealkylation catalyst can be selected to convert 98 wt % of the methylethylbenzene in reformate feed 2 to toluene, and alternately greater than 98 wt %. In at least one embodiment, the overall conversion of C9+ aromatic hydrocarbons to C6 to C8 aromatics can be greater than 98 wt % due to conversion of C9 aromatic hydrocarbons and the removal of methyl, ethyl, propyl, butyl and pentyl groups attached to C10+ aromatic hydrocarbons. Dealkylation effluent 6 can contain mixed xylenes, toluene, benzene, light gases, and C9+ aromatic hydrocarbons. Dealkylation effluent 6 can contain a greater amount of C6 to C8 aromatic hydrocarbons and a lesser amount of C9+ aromatic hydrocarbons compared to reformate feed 2. Dealkylation effluent 6 can contain a greater amount of p-xylene than reformate feed 2.

Dealkylation effluent 6 is introduced to reformate splitter 200.

Reformate splitter 200 can be any type of separation unit capable of separating a stream into its component parts. In at least one embodiment, reformate splitter 200 can be one splitter column designed to separate the feed stream into multiple split streams. In at least one embodiment, reformate splitter 200 can be multiple splitter columns in series designed to separate one component from the feed stream. In at least one embodiment, reformate splitter 200 can be one or more distillation units. The pressure across reformate splitter 200 can be in the range from 0.3 bar gauge (barg) (30 kPa) to 6 barg (600 kPa). The temperature across reformate splitter 200 can be in the range from 50 deg C. and 300 deg C. It can be understood by one of skill in the art that reformate splitter 200 can be designed to operate at a temperature and pressure to produce the desired streams, such that different stages in a single unit or different units when multiple used are deployed can operate at different temperature and pressure from the other stages or units. In at least one embodiment, where reformate splitter 200 is one distillation column, the distillation column can include multiple sections in one vessel, where each section can have different operating conditions.

Reformate splitter 200 can separate the components in dealkylation effluent 6 to produce light gases stream 8, benzene stream 10, heavy hydrocarbons stream 12, C9 aromatic hydrocarbons stream 14, xylene stream 16, and toluene stream 20.

Light gases stream 8 can contain light gases. Light gases stream 8 can be further processed to separate the light gases from hydrogen, which can be recycled to the dealkylation reactor. The light gases can be further separated. Hydrocarbon gases containing one or two carbons can be introduced to fuel gas blend. Hydrocarbon gases containing three or four carbons can be introduced to an LPG gas plant. In an alternate embodiment, light gases stream 8 can be purged to atmosphere or can be burned to produce heat.

Benzene stream 10 can contain benzene. Benzene stream 10 can be stored, alternately can be further processed, alternately introduced to transalkylation reactor 600, and alternately can be disposed.

Heavy hydrocarbons 12 can contain C10+ aromatic hydrocarbons, including C10+ aromatic hydrocarbons formed in dealkylation reactor 100 and unreacted C10+ aromatic hydrocarbons from reformate feed 2. Heavy hydrocarbons 12 can be purged from the system, alternately can be further processed to recover hydrocarbons of value, and alternately can be destroyed. Removing the C10+ aromatic hydrocarbons from the system reduces accumulation of the inert C10+ aromatic hydrocarbons through the recycle streams from splitter column 700. Removing C10+ aromatic hydrocarbons from the system can prolong the catalyst activity of the transalkylation catalyst in transalkylation reactor 600 and can improve catalyst performance.

Toluene stream 20 can contain toluene. A fraction of toluene stream 20 can be introduced to toluene disproportionation reactor 300. In at least one embodiment, toluene disproportionation reactor 300 is included when the amount of toluene in reformate feed 2 exceeds 150 wt % of the amount of trimethylbenzene. Toluene disproportionation reactor 300 can be any type of unit capable of supporting a toluene disproportionation reaction, Reaction 1.

$$2CH_3C_6H_5 \leftrightarrow C_6H_6 + (CH_3)_2C_6H_4 \quad \text{(Reaction 1)}$$

where $CH_3C_6H_5$ is toluene, $C_6H_6$ is benzene, and $(CH_3)_2C_6H_4$ is xylene. In the disproportionation reaction, a methyl group (—$CH_3$) is transferred from one toluene to another toluene to produce a benzene and a xylene. Toluene disproportionation reactor 300 can include a disproportionation catalyst. The disproportionation catalyst can be any type of catalyst capable of catalyzing reaction 1. The disproportionation temperature in toluene disproportionation reactor 300 can be between 200 degrees Celsius (deg C.) and 550 deg C. The disproportionation pressure in toluene disproportionation reactor 300 can be between 5 bar (500 kilopascal (kPa)) and 50 bar (5000 kPa) and alternately between 10 bar (1000 kPa) and 50 bar (5000 kPa). The LHSV in toluene disproportionation reactor 300 can be between 1 per hour ($hr^{-1}$) and 20 $hr^{-1}$ and alternately between 1 $hr^{-1}$ and 10 $hr^{-1}$. Reaction 1 is an equilibrium reaction with a thermodynamic limit, where the reaction can be designed to balance the production of products with reaction conditions. The reaction products can exit toluene disproportionation reactor 300 as disproportionation effluent 30. Disproportionation effluent 30 can include toluene, benzene, mixed xylenes, and combinations of the same. Disproportionation effluent 30 can be introduced to splitter column 700.

In at least one embodiment, toluene split stream 22 can be separated from toluene stream 20 and introduced to transalkylation reactor 600. Toluene split stream 22 can have a flow rate to maintain a ratio of toluene to trimethylbenzene in transalkylation reactor 600 in the range of 0.3 to 3. In at least one embodiment, when the flow rate of toluene stream 20 is insufficient to maintain a ratio of toluene to trimethylbenzene in the range of 0.3 to 3, an alternate stream of toluene can be introduced to transalkylation reactor 600. Maintaining the ratio of toluene to trimethylbenzene in the range of 0.3 to 3 increases the production of xylene, alternately in the range of 0.5 to 1.5, and alternately in the range of 0.8 to 1.2. Maintaining the ratio of toluene to trimethylbenzene close to 1 results in greater selectivity of xylene in the product.

Figure 2:
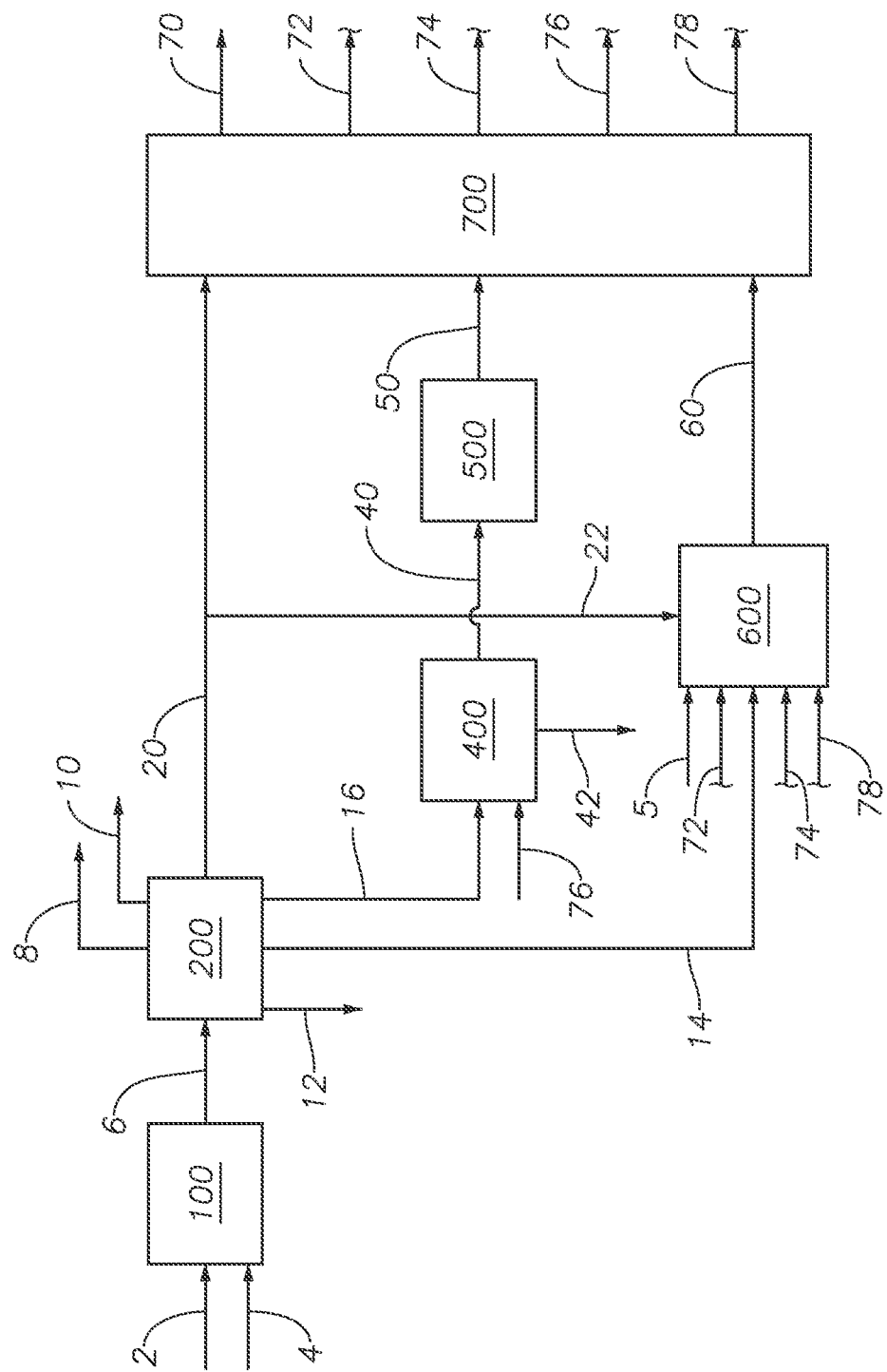
FIG. 2 provides a process diagram of an embodiment of the process.

In at least one embodiment, as shown in FIG. 2, the process to maximize xylene production is in the absence of toluene disproportionation reactor 300. In a process in the absence of toluene disproportionation reactor 300 any excess toluene not separated in toluene split stream 22 can be introduced to splitter column 700. In at least one embodiment, the entire flow of toluene stream 20 is introduced to transalkylation reactor 600 through toluene split stream 22.

Xylene stream 16 can contain mixed xylenes. Xylene stream 16 can be introduced to p-xylene separation unit 400. P-xylene separation unit 400 can be any type of separation unit capable of separating p-xylene from a stream containing mixed xylenes. Examples of p-xylene separation unit 400 can include a crystallization unit or an adsorption unit. P-xylenes are separated from xylene stream 16 in p-xylene separation unit 400 to produce p-xylene depleted stream 40 and p-xylene product 42. P-xylene product 42 can contain p-xylene. P-xylene product 42 can be stored, alternately can be further processed, and alternately can be used as finished product stream. P-xylene depleted stream 40 can contain m-xylene and o-xylene. P-xylene depleted stream 40 can be introduced to isomerization unit 500.

P-xylene separation unit 400 cannot be used to separate components other than p-xylene; one of skill in the art will appreciate that a p-xylene. Advantageously, separating C9 aromatics stream 14 upstream of p-xylene separation unit 400 increases the effectiveness of separating p-xylene from xylene stream 16 in p-xylene separation unit 400.

Isomerization unit 500 can be any type of unit capable of supporting xylene isomerization reactions, including associated units and instrumentation. Isomerization unit can include an isomerization catalyst. The isomerization catalyst can be any type of catalyst capable of catalyzing the isomerization reaction of m-xylene and o-xylene to p-xylene. Examples of the isomerization catalyst can include a surface modified zeolite catalyst such as a zeolite beta, an HZSM-5, an MCM-49, and ZSM-12. The isomerization temperature in isomerization unit 500 can be between 200 degrees Celsius (deg C.) and 550 deg C. The isomerization pressure in isomerization unit 500 can be between 5 bar (500 kilopascal (kPa)) and 50 bar (5000 kPa) and alternately between 10 bar and 50 bar. The LHSV in isomerization unit 500 can be between 1 per hour ($hr^{-1}$) and 20 $hr^{-1}$ and alternately between 1 $hr^{-1}$ and 10 $hr^{-1}$. The mixed xylenes produced in isomerization unit 500 can exit as isomerization effluent 50. Isomerization effluent 50 can be introduced to splitter column 700.

C9 aromatics stream 14 can contain C9 aromatic hydrocarbons, including C9 aromatic hydrocarbons formed in dealkylation reactor 100 and unreacted C9 aromatic hydrocarbons from reformate feed 2. In at least one embodiment, C9 aromatics stream 14 is in the absence of C10+ aromatic hydrocarbons. In at least one embodiment, C9 aromatics stream 14 contains less than 5 wt % C10+ aromatic hydrocarbon. C9 aromatics stream 14 along with hydrogen stream 5 can be introduced to transalkylation reactor 600.

Hydrogen stream 5 can be any stream containing hydrogen gas. Hydrogen stream 5 can be a stream of pure hydrogen from a fresh hydrogen source. In at least one embodiment, hydrogen gas can be recovered from another part of the process and can be recycled as hydrogen stream 5 and introduced to transalkylation reactor 600. Hydrogen stream 5 can be from a hydrogen source in a refinery and can contain light hydrocarbons.

Transalkylation reactor 600 can be a fixed bed reactor or a fluidized bed reactor. The transalkylation temperature in transalkylation reactor 600 can be between 200 deg C. and 550 deg C. The transalkylation pressure in transalkylation reactor 600 can be between 5 bar (500 kPa) and 50 bar (5000 kPa), alternately 10 bar (1000 kPa) and 50 bar (5000 kPa), and alternately 10 bar (1000 kPa) and 40 bar (4000 kPa). The LHSV can be between 0.2 $hr^{-1}$ and 20 $hr^{-1}$ and alternately between 0.5 $hr^{-1}$ and 6 $hr^{-1}$. The volumetric flow ratio of hydrogen gas to hydrocarbons can be in the range of 0 to 8. The operating conditions can be set to maximize the production of xylenes. The temperature can have a greater influence on the transalkylation reaction than pressure. It is understood that higher temperatures, higher pressures, and lower LHSV favor transalkylation reactions, while higher temperatures can lead to catalyst deactivation and therefore, the operating conditions must be balanced to maximize production and minimize catalyst deactivation. Due to the conversion of C9+ aromatic hydrocarbons in dealkylation reactor 100, the loading on transalkylation reactor can be reduced.

Transalkylation reactor 600 can include a transalkylation catalyst. The transalkylation catalyst can include any catalyst capable of catalyzing transalkylation reactions. Examples of transalkylation catalysts include bifunctional catalysts as described in U.S. Pat. No. 5,866,741. The transalkylation catalyst can be selected to selectively convert one or more of the C9+ aromatic hydrocarbons over the others in transalkylation reactions. In at least one embodiment, the transalkylation catalyst can be selected to selectively convert trimethylbenzenes to mixed xylenes. Advantageously, using a catalyst designed to catalyze transalkylation reactions increases the efficiency and performance as compared to a catalyst designed to perform transalkylation, disproportionation and isomerization. Using a catalyst targeted to transalkylation reactions increases the production of mixed xylenes.

There are two primary reactions that occur in transalkylation reactor 600 to form mixed xylenes. One reaction is Reaction 1 described here. The second reaction is an equilibrium transalkylation reaction of toluene and trimethylbenzene:

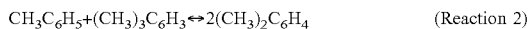

$$CH_3C_6H_5 + (CH_3)_3C_6H_3 \leftrightarrow 2(CH_3)_2C_6H_4 \quad \text{(Reaction 2)}$$

where $CH_3C_6H_5$ is toluene, $(CH_3)_3C_6H_3$ is trimethylbenzene, and $2(CH_3)_2C_6H_4$ is xylene. In addition to the two primary reactions, other transalkylation reactions can convert C9+ aromatic hydrocarbons to toluene, benzene, mixed xylenes, and light gases. The reaction products produced in transalkylation reactor 600 can exit as transalkylation effluent 60. Transalkylation effluent 60 can contain mixed xylenes, toluene, benzene, light gases, and C9+ aromatic hydrocarbons. The C9+ aromatic hydrocarbons in transalkylation effluent 60 can include C9+ aromatic hydrocarbons formed in transalkylation reactor, C9+ aromatic hydrocarbons formed in the dealkylation reactor, and C9+ aromatic hydrocarbons from reformate feed 2. Transalkylation effluent 60 can be introduced to splitter column 700.

Splitter column 700 can be any type of separation unit capable of separating a stream into its components. Splitter column 700 can be any type of separation unit capable of separating a stream into its component parts. In at least one embodiment, splitter column 700 can be one splitter column designed to separate the feed stream into multiple split streams. In at least one embodiment, splitter column 700 can be multiple splitter columns in series designed to separate one component from the feed stream. In at least one embodiment, splitter column 700 can be one or more distillation units. The pressure across splitter column 700 can be in the range from 0.3 bar gauge (barg) (30 kPa) to 6 barg (600 kPa). The temperature across splitter column 700 can be in the range from 50 deg C. and 300 deg C. It can be understood by one of skill in the art that splitter column 700 can be designed to operate at a temperature and pressure to produce the desired streams, such that different stages in a single unit or different units when multiple used are deployed can operate at different temperature and pressure from the other stages or units. In at least one embodiment, where splitter column 700 is one distillation column, the distillation column can include multiple sections in one vessel, where each section can have different operating conditions.

Splitter column 700 can separate the components in disproportionation effluent 30, isomerization effluent 50, and transalkylation effluent 60 to produce separated light gases 70, benzene recycle 72, toluene recycle 74, xylene recycle 76, and C9+ aromatics recycle 78. Separated light gases 70 can be processed further or stored. Separated light gases 70 can be processed further or stored. Benzene recycle 72, toluene recycle 74, and C9+ aromatics recycle 78 can be recycled to transalkylation reactor 600. Xylene recycle 76 can be recycled to p-xylene separation unit 400. Adding benzene from benzene recycle 72 to transalkylation reactor 600 can drive the equilibrium toward of benzene through Reaction 1, which reduces the consumption of toluene in Reaction 1. By reducing the consumption of toluene, more toluene is available for production of mixed xylenes through Reaction 2. The amount of benzene added through benzene recycle 72 can be in the range between 1 wt % and 10 wt %. The amount of benzene added through benzene recycle 72 can be a function of the transalkylation temperature in transalkylation reactor 600, and therefore, the transalkylation temperature can be monitored with temperature sensors or other instrumentation, such that the flow rate of benzene recycle 72 can be adjusted across the run in transalkylation reactor 600. In at least one embodiment, the transalkylation temperature is different at the beginning of the run and at the end of the run. In at least one embodiment, benzene stream 10 can be introduced to 600 transalkylation reactor to maintain the thermodynamic equilibrium.

C9+ aromatics recycle 78 can contain an amount of C10 hydrocarbons that does not participate in any of the reactions in transalkylation reactor 600. In at least one embodiment, C9+ aromatics recycle 78 can include trace amounts of C11 hydrocarbons and trace amounts of C12 hydrocarbons. A slip stream from C9+ aromatics recycle 78 can be purged from the system to prevent build up in the loop between transalkylation reactor 600 and splitter column 700.

The yield of p-xylene in p-xylene product 42 is in the range between 75 wt % and 82 wt %.

Figure 3:
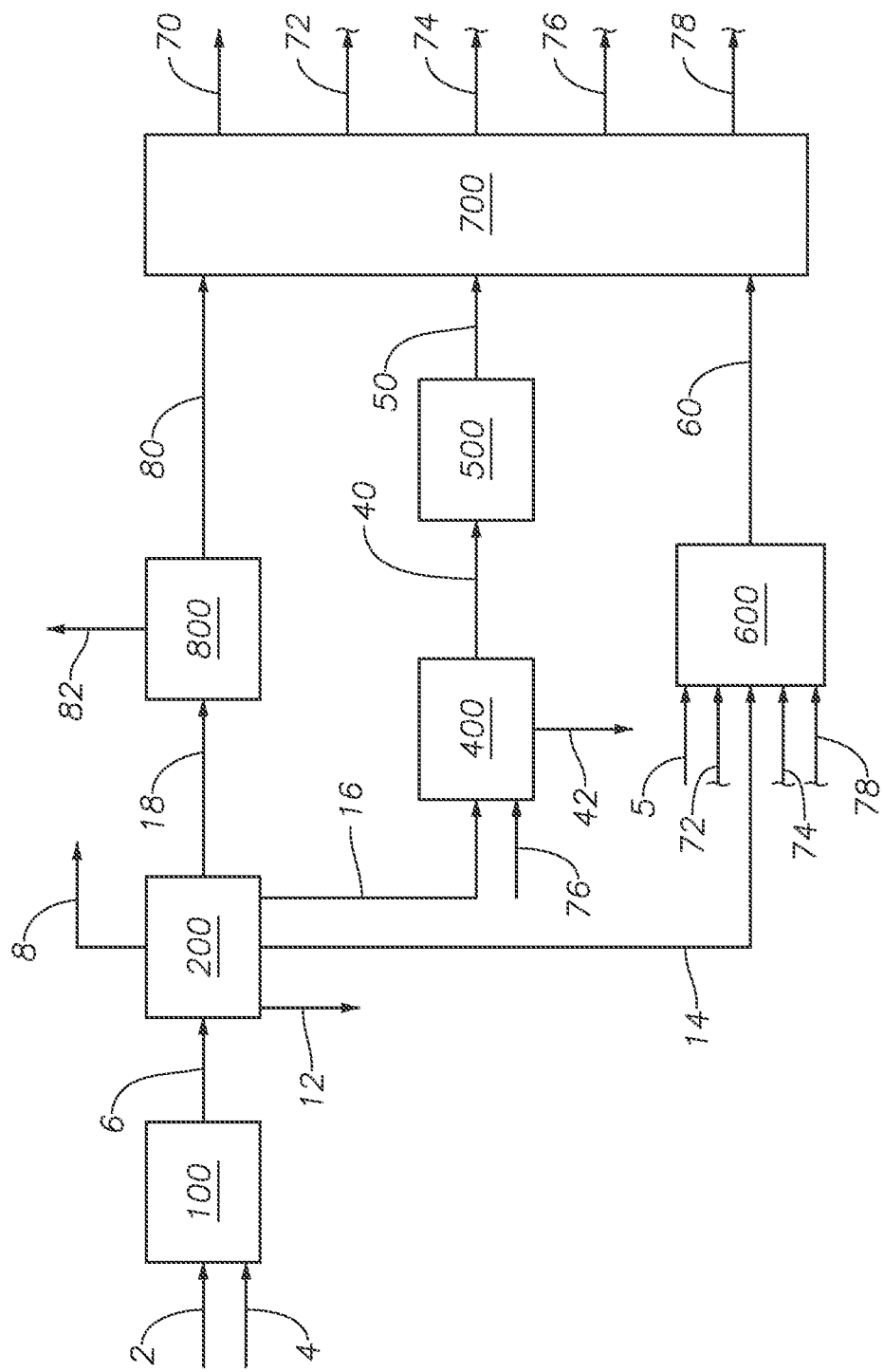
FIG. 3 provides a process diagram of an embodiment of the process.

Referring to FIG. 3, an alternate embodiment of the process to maximize production of xylenes is provided with reference to FIG. 1. Mixed light aromatics stream 18 can be separated in reformate splitter 200. Mixed light aromatics stream 18 can include toluene, benzene, non-aromatics and combinations of the same. Mixed light aromatics stream 18 can further include non-aromatics. Mixed light aromatics stream 18 can be introduced to aromatic extraction unit 800.

Aromatic extraction unit 800 can be any type of extraction unit capable of separating aromatic components from other components in a stream. Examples of aromatic extraction unit can include liquid-liquid extraction and extractive distillation, both of which use solvents. Examples of solvents suitable for use in aromatic extraction unit 800 can include sulfolane ($C_4H_8O_2S$), furfural ($C_5H_4O_2$), tetraethylene glycol ($C_8H_{18}O_5$), dimethylsulfoxide ($C_2H_6OS$), and N-methyl-2-pyrrolidone ($C_5H_9NO$). The particular conditions in aromatic extraction unit 800 depend on the type of extraction technology selected. Aromatic extraction unit 800 can be included in embodiments where the concentration of non-aromatics is at a level that can disrupt the function or performance of the units of the system.

Non-aromatic hydrocarbons in mixed light aromatics stream 18 can be separated in aromatic extraction unit 800 to produce non-aromatics raffinate stream 82 and aromatics extract stream 80. Aromatics extract stream 80 can include toluene, benzene, and combinations of the same. Non-aromatics raffinate stream 82 can include non-aromatics. Removing non-aromatics can remove the non-aromatics from the downstream units and reduce dilution of the reactants in the downstream units, including transalkylation reactor 600 and p-xylene separation unit 400. Advantageously, aromatic extraction unit 800 separates non-aromatics that are not separable from C6 and C7 aromatics in reformate splitter 200. Non-aromatic hydrocarbons can include paraffins, iso-paraffins, naphthenes, and combinations of the same.

In at least one embodiment of the process according to FIG. 3, a portion of benzene recycle 72 can be purged from the system, while the remainder is introduced to transalkylation reactor 600. As noted above with respect to FIG. 1, the amount of benzene added through benzene recycle 72 can be adjusted based on the reaction conditions in transalkylation reactor 600 to optimize the production of mixed xylenes. Purging a portion of benzene recycle 72 provides a method for controlling the amount of benzene added through benzene recycle 72, avoids accumulating excess benzene in the system, and prevents dilution of the reactants in transalkylation reactor 600. A portion of benzene recycle 72 can be purged when benzene recycle 72 contains more benzene that is required to drive the equilibrium reactions in transalkylation reactor 600.

Figure 4:
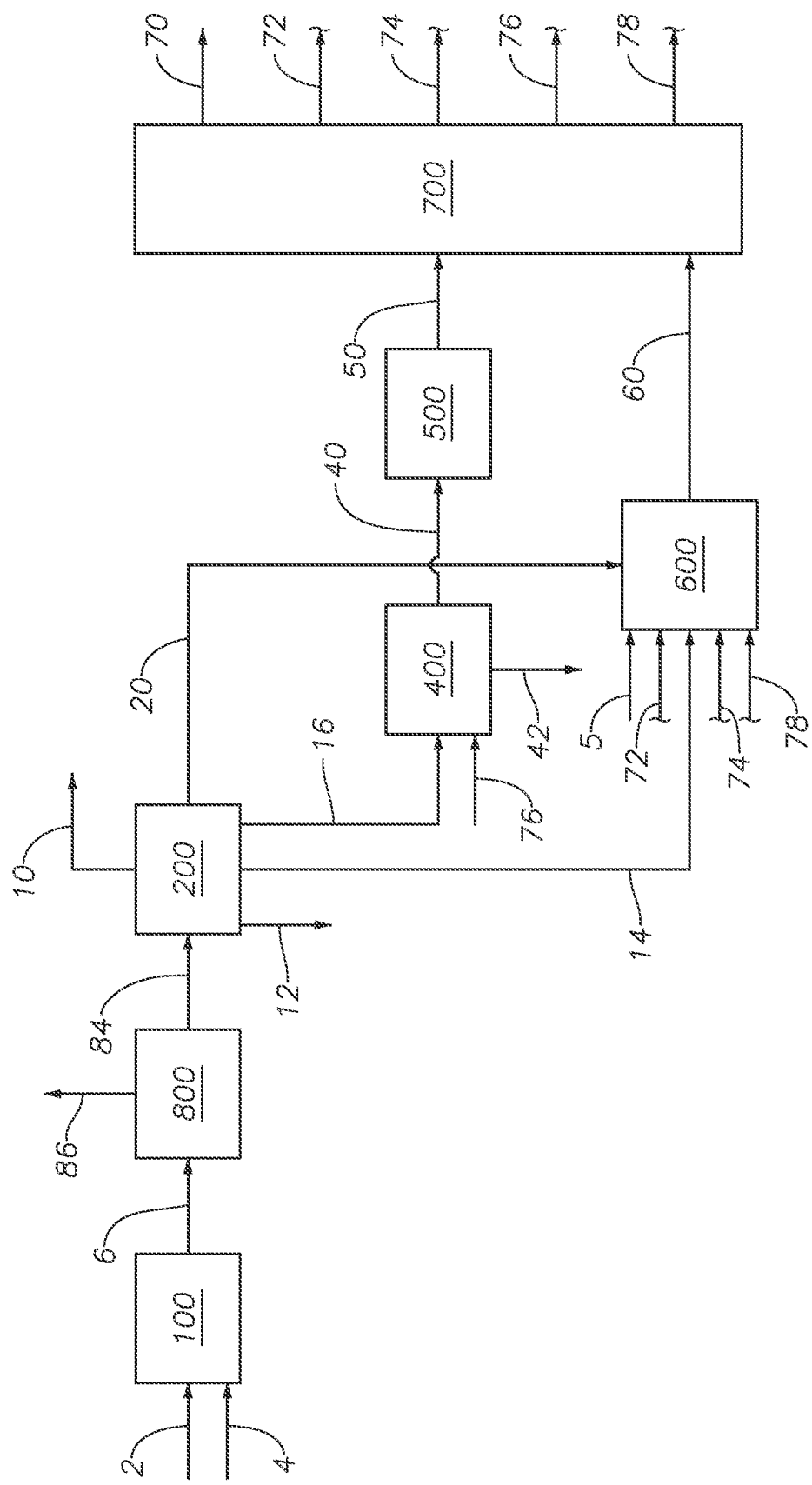
FIG. 4 provides a process diagram of an embodiment of the process.

Referring to FIG. 4, an alternate embodiment of the process to maximize production of xylenes is provided with reference to FIG. 1 and FIG. 3. Dealkylation effluent 6 is introduced to aromatic extraction unit 800. Non-aromatics in dealkylation effluent 6 can be separated in aromatic extraction unit 800 to produce aromatic feed 84 and raffinate effluent 86. Raffinate effluent 86 can include the non-aromatics separated from dealkylation effluent 6, including light hydrocarbons. Aromatic feed 84 can include C6 to C9 aromatic hydrocarbons produced in dealkylation effluent 100 and aromatic hydrocarbons present in reformate feed 2.

Aromatic feed 84 can be introduced to reformate splitter 200 to produce benzene stream 10, heavy hydrocarbons 12, C9 aromatic hydrocarbons stream 14, xylene stream 16, and toluene stream 20. Toluene stream 20, in whole, can be introduced to transalkylation reactor 600.

Figure 6:
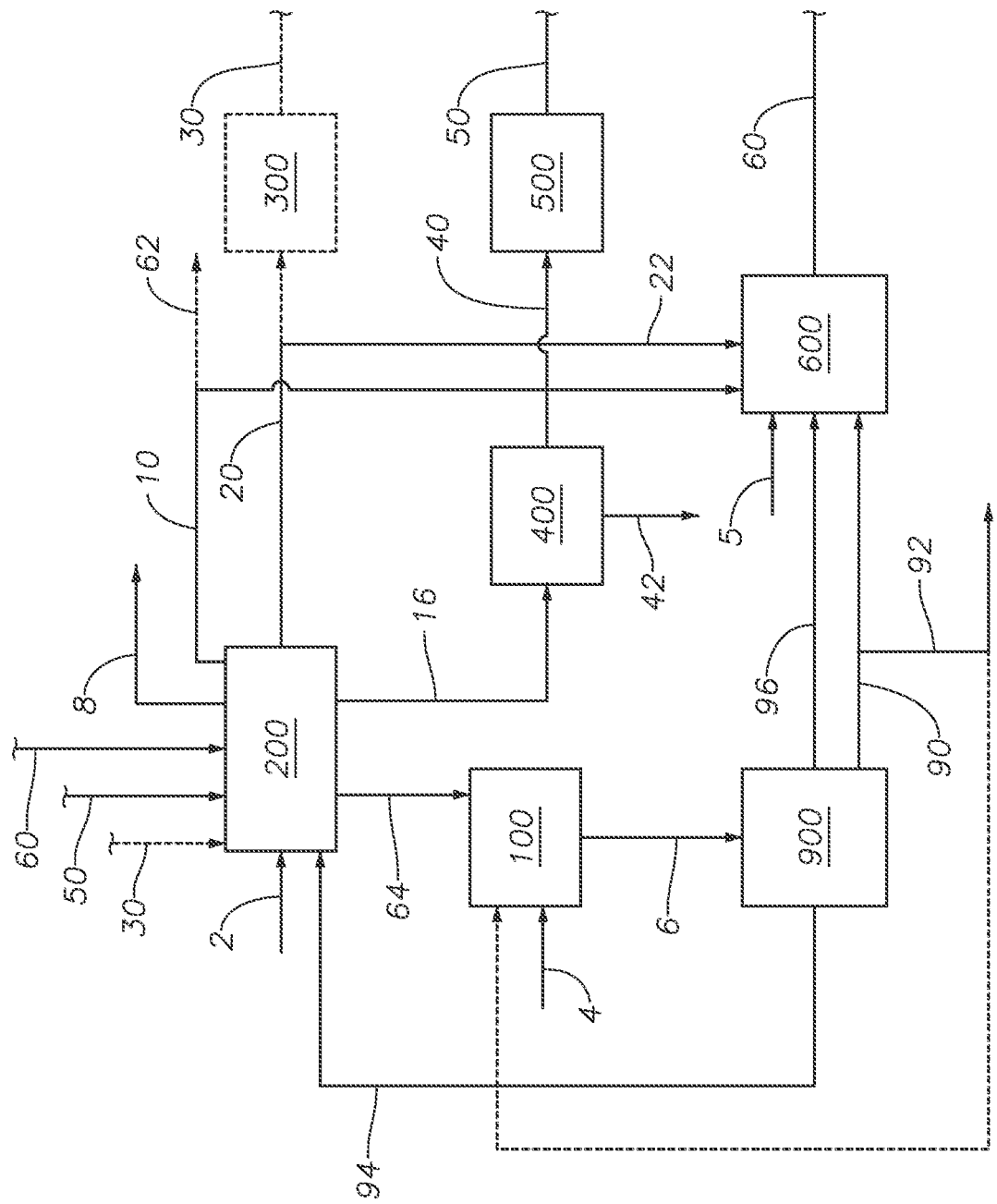
FIG. 6 provides a process diagram of an embodiment of the process.

Referring to FIG. 6, an alternate embodiment of the process to maximize production of xylenes is provided with reference to FIG. 1. Reformate feed 2 is introduced to reformate splitter 200. Reformate splitter 200 can separate the components in reformate feed 2 to produce light gases stream 8, benzene stream 10, combined heavy stream 64, xylene stream 16, and toluene stream 20. Separating the reformate stream can reduce the load in dealkylation reactor 100. Benzene and toluene do not react in dealkylation reactor 100 and therefore, removing them from the reactor enhances catalyst performance by reducing dilution. Combined heavy stream 64 can include the C9+ aromatic hydrocarbons present in reformate feed 2 and the trace amount of C9+ aromatic hydrocarbons produced in transalkylation reactor 600.

Combined heavy stream 64 can be introduced to dealkylation reactor 100. Hydrogen feed 4 can be introduced to dealkylation reactor 100. Dealkylation reactor 100 operates as described with reference to FIG. 1. The inclusion of dealkylation reactor 100 can increase the amount of xylenes produced by increasing conversion of C10+ aromatic hydrocarbons.

Dealkylation effluent 6 can be introduced to dealkylation splitter 900. Dealkylation splitter 900 can separate the components in dealkylation effluent 6 to produce light recycle stream 94, C9 stream 96, and C10+ aromatics stream 90. Light recycle stream 94 can contain light gases, benzene, toluene, xylenes, and combinations of the same. Light recycle stream 94 can be recycled to reformate splitter 200. C10+ aromatics stream 90 can contain C10+ aromatic hydrocarbons. C10+ stream 90 can be introduced to transalkylation reactor 600. Introducing C10+ stream 90 to transalkylation reactor 600 can maintain the desired thermodynamics in transalkylation reactor 600. A purge stream can be separated from C10+ stream 90 as purge stream 92. The flow rate of purge stream 92 can be determined based on the overall volumetric flow rate of C10+ stream 90. The flow rate of purge stream 92 can be optimized to reduce loading of C10+ aromatic hydrocarbons in transalkylation reactor 600. Reduced loading can increase the conversion of MEB to toluene in transalkylation reactor 600. In at least one embodiment, the conversion rate of MEB in transalkylation reactor 600 is equal to or greater than 98%. Additionally, reduced loading can reduce fouling of the transalkylation catalyst in transalkylation reactor 600 prolonging the run time of transalkylation reactor 600 and can reduce the size of transalkylation reactor 600. In at least one embodiment, the entire volumetric flow rate of C10+ stream 90 flows out through purge stream 92. In at least one embodiment, the entire volumetric flow rate of C10+ stream 90 is introduced to transalkylation reactor 600.

Optionally, in at least one embodiment, purge stream 92 can be recycled to dealkylation reactor 100. The hydrogen pressure and severity of the operation conditions can be adjusted to achieve full conversion of the C10+ aromatic hydrocarbons to C9 aromatic hydrocarbons and compounds with less than 9 carbon atoms.

C10+ stream 90 can be introduced to transalkylation reactor 600 along with C9 stream 96, benzene stream 10, and toluene split stream 22. As described with reference to FIG. 1, hydrogen stream 5 can be introduced to transalkylation reactor 600. In the embodiment described with reference to FIG. 6, the entire volumetric flow of benzene stream 10 is introduced to transalkylation reactor 600. Benzene stream 10 can be introduced to transalkylation reactor 600 to maintain the thermodynamic equilibrium, which drives conversion of toluene to xylenes. The presence of benzene can drive equilibrium toward other reaction products, such as xylenes. Optionally, in certain embodiments, a portion of benzene stream can be separated as benzene split stream 62. The volumetric flow of benzene split stream 62 can be determined by the improved xylene yield. The amount of benzene introduced to the transalkylation reactor through benzene stream 10 can be in the range between 0.01 wt % and 5 wt % with the remaining amount removed from the system through benzene split stream 62.

In the embodiment described with reference to FIG. 6, the entire volumetric flow of toluene stream 20 is introduced to transalkylation reactor 600 through toluene split stream 22. Optionally, in certain embodiments, a portion of toluene stream 20 can be introduced to toluene disproportionation reactor 300. Toluene disproportionation reactor 300 can be included when the amount of toluene in reformate feed 2 exceeds 150 wt % of the amount of trimethylbenzene. In the embodiments that include toluene disproportionation reactor 300, the volumetric flow rate of toluene split stream 22 can be adjusted to maintain a ratio of toluene to trimethylbenzene in the range of 0.3 to 3 in transalkylation reactor 600. Toluene disproportionation reactor 300 operates as described with reference to FIG. 1. In embodiments where toluene disproportionation reactor 300 is present, disproportionation effluent 30 can be recycled to reformate splitter 200.

Transalkylation reactor 600 operates as described with reference to FIG. 1. Transalkylation effluent 60 can be introduced to reformate splitter 200. Isomerization effluent 50, produced as described with reference to FIG. 1, can be recycled to reformate splitter 200.

Using reformate splitter 200 to separate components in disproportionation effluent 30, isomerization effluent 50, and transalkylation effluent 60 can reduce complexity of the system. In an alternate embodiment, disproportion effluent 30, isomerization effluent 50, and transalkylation effluent 60 can be introduced to splitter column 700 as described with respect to FIG. 1.

Advantageously, the position of the dealkylation reactor upstream of the transalkylation produces toluene not present in the heavy reformate feed, toluene is a reactant in transalkylation reactions to produce xylene, thus a process with the dealkylation reactor upstream of the transalkylation increases xylene production. Advantageously, the position of the dealkylation reactor upstream of the transalkylation reactor reduces the amount of C9 aromatic hydrocarbons and C10+ aromatic hydrocarbons being introduced to the transalkylation reactor.

Advantageously, the use of both a reformate splitter and a splitter column increase the ability to control the recycle of components to the transalkylation reactor. Advantageously, the use of both a reformate splitter and a splitter column means that the splitter column handles only aromatic hydrocarbons, while the reformate splitter handles both the aromatic hydrocarbons and non-aromatic hydrocarbons.

Both the dealkylation reactor and the transalkylation reactor are in the absence of methanol and in the absence of methylation reactions, which are irreversible reactions that add a methyl group to a compound. In at least one embodiment, the heavy reformate feed is in the absence of ethylbenzene. The process to maximize xylene production is in the absence of a debutanizer. The process to maximize xylene production is in the absence of a depheptanizer. In at least one embodiment, the system for producing p-xylene is in the absence of a hydrogenation reaction or hydrogenation reactor, where a hydrogenation reaction reactor refers to a reaction that generally adds hydrogen to a hydrocarbon for the purposes of saturating the hydrocarbon. In at least one embodiment, the system is in the absence of a hydrodealkylation reaction or a hydrodealkylation reactor, where a hydrodealkylation reaction is a reaction that involves the detachment of an alkyl group from an aromatic ring.

Dealkylation reactor 100 is not a reforming unit. A reforming unit converts naphthas into an aromatic hydrocarbons-rich product over a platinum-containing catalyst at high temperatures and hydrogen pressure. A reforming unit has the goal of increasing the octane number of the hydrocarbon feed stream to the reforming unit. The primary reactions in a reforming unit are dehydrogenation reactions and cracking reactions.

EXAMPLES

The following examples were carried out using a simulation program.

Example 1 was simulated as the process for maximizing xylene production according to FIG. 1. The process was simulated using ASPEN. The process for maximizing xylene production includes a dealkylation reactor, a transalkylation reactor, p-xylene separation and xylene isomerization.

TABLE 1

| Composition and flow rates for Example 1 | | | | | | | | | | | | | | |
|---|---|---|---|---|---|---|---|---|---|---|---|---|---|---|
| | | 2 | 4 | 6 | 8 | 10 | 12 | 14 | 16 | 20 | 22 | 30 | 40 | 42 |
| Mass Flow | | 1598 | 10 | 1608 | 86 | 73 | 73 | 506 | 497 | 373 | 369 | 4 | 4544 | 1320 |
| Hydrogen | kg/hr | 0 | 10 | 7 | 7 | 0 | 0 | 0 | 0 | 0 | 0 | 0 | 0 | 0 |
| Light Gas | kg/hr | 0 | 0 | 79 | 79 | 0 | 0 | 0 | 0 | 0 | 0 | 0 | 0 | 0 |
| Benzene | kg/hr | 49 | 0 | 73 | 0 | 73 | 0 | 0 | 0 | 0 | 0 | 2 | 0 | 0 |
| Toluene | kg/hr | 213 | 0 | 373 | 0 | 0 | 0 | 0 | 0 | 373 | 369 | 0 | 0 | 0 |
| p-xylene | kg/hr | 97 | 0 | 119 | 0 | 0 | 0 | 0 | 119 | 0 | 0 | 1 | 0 | 1320 |
| o-xylene & m-xylene | kg/hr | 291 | 0 | 378 | 0 | 0 | 0 | 0 | 378 | 0 | 0 | 1 | 4544 | 0 |
| MEB | kg/hr | 211 | 0 | 3 | 0 | 0 | 0 | 3 | 0 | 0 | 0 | 0 | 0 | 0 |
| TMB | kg/hr | 565 | 0 | 503 | 0 | 0 | 0 | 503 | 0 | 0 | 0 | 0 | 0 | 0 |
| C10+ | kg/hr | 171 | 0 | 73 | 0 | 0 | 73 | 0 | 0 | 0 | 0 | 0 | 0 | 0 |

| | | 50 | 5 | 60 | 70 | 72 | 74 | 76 | 78 |
|---|---|---|---|---|---|---|---|---|---|
| Mass Flow | | 4544 | 100 | 2265 | 156 | 67 | 649 | 5367 | 573 |
| Hydrogen | kg/hr | 0 | 100 | 96 | 96 | 0 | 0 | 0 | 0 |
| Light Gas | kg/hr | 0 | 0 | 61 | 61 | 0 | 0 | 0 | 0 |
| Benzene | kg/hr | 0 | 0 | 65 | 0 | 67 | 0 | 0 | 0 |
| Toluene | kg/hr | 0 | 0 | 649 | 0 | 0 | 649 | 0 | 0 |
| p-xylene | kg/hr | 1045 | 0 | 156 | 0 | 0 | 0 | 1201 | 0 |
| o-xylene & m-xylene | kg/hr | 3499 | 0 | 666 | 0 | 0 | 0 | 4166 | 0 |
| MEB | kg/hr | 0 | 0 | 3 | 0 | 0 | 0 | 0 | 3 |
| TMB | kg/hr | 0 | 0 | 503 | 0 | 0 | 0 | 0 | 503 |
| C10+ | kg/hr | 0 | 0 | 67 | 0 | 0 | 0 | 0 | 67 |

Example 2

Figure 5:
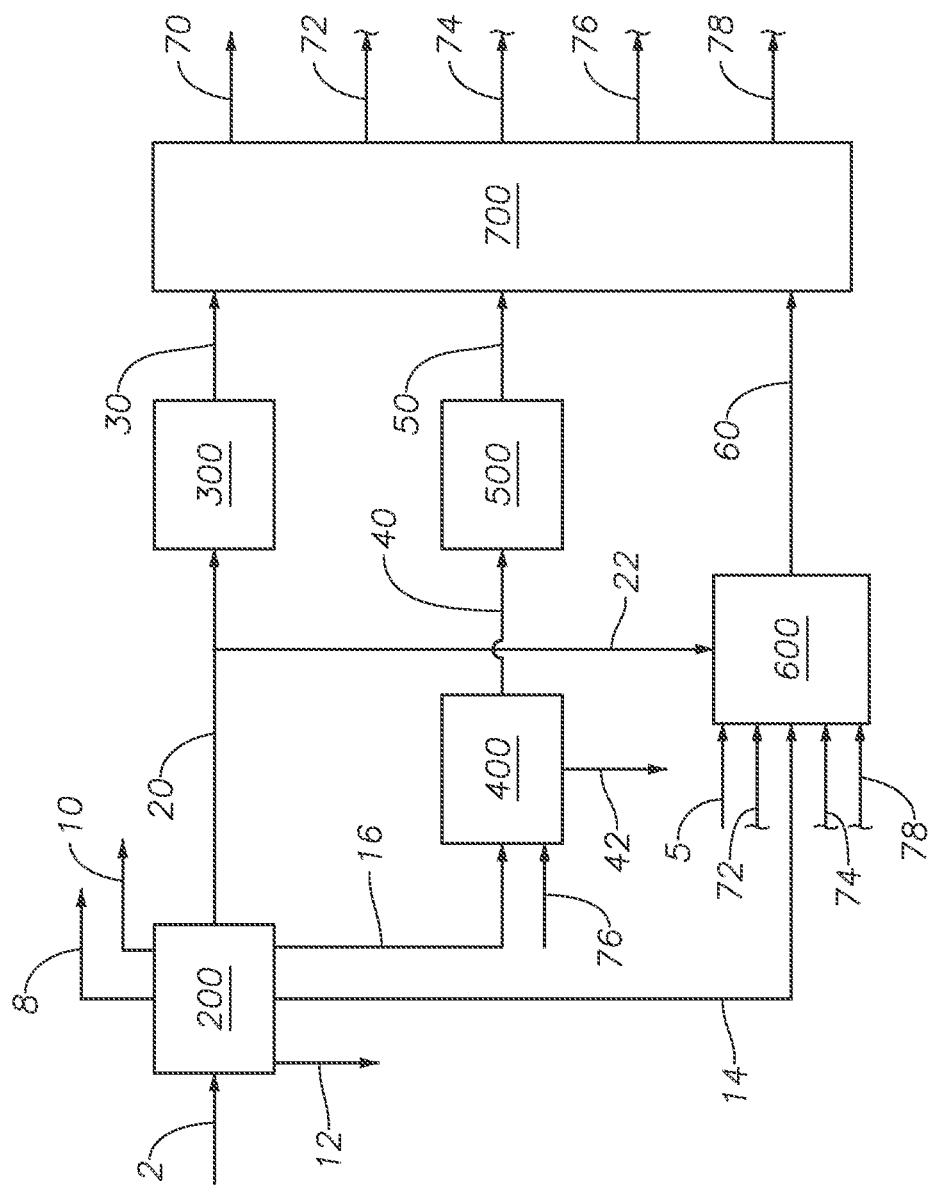
FIG. 5 provides a process diagram of the process for Example 2.

Example 2 is a comparative example in the absence of a dealkylation reactor. The process was simulated according to the process of FIG. 5. FIG. 5 depicts a process in the absence of dealkylation reactor 100, where reformate feed 2 is introduced directly to reformate splitter 200.

TABLE 2

| Composition and flow rates for Example 2. | | | | | | | | | | | |
|---|---|---|---|---|---|---|---|---|---|---|---|
| | | 2 | 10 | 12 | 14 | 16 | 20 | 22 | 30 | 40 | 42 |
| Mass Flow | | 1598 | 49 | 146 | 802 | 388 | 213 | 211 | 2 | 4439 | 1290 |
| Hydrogen | kg/hr | 0 | 0 | 0 | 0 | 0 | 0 | 0 | 0 | 0 | 0 |
| Light Gas | kg/hr | 0 | 0 | 0 | 0 | 0 | 0 | 0 | 0 | 0 | 0 |
| Benzene | kg/hr | 49 | 49 | 0 | 0 | 0 | 0 | 0 | 1 | 0 | 0 |
| Toluene | kg/hr | 213 | 0 | 0 | 0 | 0 | 213 | 211 | 0 | 0 | 0 |
| p-xylene | kg/hr | 97 | 0 | 0 | 0 | 97 | 0 | 0 | 0 | 0 | 1290 |
| o-xylene & m-xylene | kg/hr | 291 | 0 | 0 | 0 | 291 | 0 | 0 | 1 | 4439 | 0 |
| MEB | kg/hr | 211 | 0 | 0 | 211 | 0 | 0 | 0 | 0 | 0 | 0 |
| TMB | kg/hr | 565 | 0 | 0 | 565 | 0 | 0 | 0 | 0 | 0 | 0 |
| C10+ | kg/hr | 171 | 0 | 146 | 25 | 0 | 0 | 0 | 0 | 0 | 0 |

| | | 50 | 5 | 60 | 70 | 72 | 74 | 76 | 78 |
|---|---|---|---|---|---|---|---|---|---|
| Mass Flow | | 4439 | 100 | 2486 | 214 | 73 | 449 | 5342 | 851 |
| Hydrogen | kg/hr | 0 | 100 | 93 | 93 | 0 | 0 | 0 | 0 |
| Light Gas | kg/hr | 0 | 0 | 120 | 120 | 0 | 0 | 0 | 0 |
| Benzene | kg/hr | 0 | 0 | 72 | 0 | 73 | 0 | 0 | 0 |
| Toluene | kg/hr | 0 | 0 | 449 | 0 | 0 | 449 | 0 | 0 |
| p-xylene | kg/hr | 1021 | 0 | 172 | 0 | 0 | 0 | 1193 | 0 |
| o-xylene & m-xylene | kg/hr | 3418 | 0 | 729 | 0 | 0 | 0 | 4148 | 0 |
| MEB | kg/hr | 0 | 0 | 211 | 0 | 0 | 0 | 0 | 211 |
| TMB | kg/hr | 0 | 0 | 565 | 0 | 0 | 0 | 0 | 565 |
| C10+ | kg/hr | 0 | 0 | 74 | 0 | 0 | 0 | 0 | 74 |

Comparing the results of Example 1 and Example 2 shows that the addition of dealkylation reactor 100 reduces the flow rate of C9 aromatic hydrocarbons introduced to transalkylation reactor by 9.1%. In part the reduced flow rate is due to the conversion of methylethylbenzene to toluene in dealkylation reactor 100 in the process to maximize xylenes as embodied in FIG. 1. In addition, the results indicate that the addition of dealkylation reactor 100 increases the conversion of C10+ aromatic hydrocarbons to C6 to C8 aromatic hydrocarbons, where the non-converted compounds can be purged from the system as part of heavy hydrocarbons 12.

Example 3

Example 3 is an example of a simulated process described with reference to FIG. 6. FIG. 6. includes dealkylation reactor 100 downstream from reformate splitter 200.

TABLE 3

Composition and flow rates for Example 3.

| | | 2 | 8 | 10 | 62 | 20 | 22 | 16 | 64 | 6 | 90 | 92 | 94 |
|---|---|---|---|---|---|---|---|---|---|---|---|---|---|
| Mass Flow | | 1598 | 140 | 148 | 74 | 932 | 923 | 5884 | 1462 | 1470 | 103 | 76 | 458 |
| Hydrogen | kg/hr | 0 | 7 | 0 | 0 | 0 | 0 | 0 | 0 | 3 | 0 | 0 | 3 |
| Light Gas | kg/hr | 0 | 133 | 0 | 0 | 0 | 0 | 0 | 0 | 59 | 0 | 0 | 59 |
| Benzene | kg/hr | 49 | 0 | 148 | 74 | 0 | 0 | 0 | 0 | 37 | 0 | 0 | 37 |
| Toluene | kg/hr | 213 | 0 | 0 | 0 | 932 | 923 | 0 | 0 | 161 | 0 | 0 | 161 |
| p-xylene | kg/hr | 97 | 0 | 0 | 0 | 0 | 0 | 1325 | 0 | 39 | 0 | 0 | 39 |
| o-xylene & m-xylene | kg/hr | 291 | 0 | 0 | 0 | 0 | 0 | 4558 | 0 | 159 | 0 | 0 | 159 |
| MEB | kg/hr | 211 | 0 | 0 | 0 | 0 | 0 | 0 | 212 | 3 | 0 | 0 | 0 |
| TMB | kg/hr | 565 | 0 | 0 | 0 | 0 | 0 | 0 | 1019 | 907 | 0 | 0 | 0 |
| C10+ | kg/hr | 171 | 0 | 0 | 0 | 0 | 0 | 0 | 231 | 103 | 103 | 76 | 0 |

| | | 96 | 4 | 5 | 42 | 40 | 50 | 30 | 60 |
|---|---|---|---|---|---|---|---|---|---|
| Mass Flow | | 909 | 8 | 8 | 1325 | 4558 | 4558 | 9 | 1942 |
| Hydrogen | kg/hr | 0 | 8 | 8 | 0 | 0 | 0 | 0 | 4 |
| Light Gas | kg/hr | 0 | 0 | 0 | 0 | 0 | 0 | 0 | 73 |
| Benzene | kg/hr | 0 | 0 | 0 | 0 | 0 | 0 | 4 | 58 |
| Toluene | kg/hr | 0 | 0 | 0 | 0 | 0 | 0 | 0 | 558 |
| p-xylene | kg/hr | 0 | 0 | 0 | 1325 | 0 | 1048 | 2 | 139 |
| o-xylene & m-xylene | kg/hr | 0 | 0 | 0 | 0 | 4558 | 3510 | 4 | 595 |
| MEB | kg/hr | 3 | 0 | 0 | | 0 | 0 | 0 | 1 |
| TMB | kg/hr | 907 | 0 | 0 | 0 | 0 | 0 | 0 | 453 |
| C10+ | kg/hr | 0 | 0 | 0 | 0 | 0 | 0 | 0 | 60 |

Example 4

Figure 7:
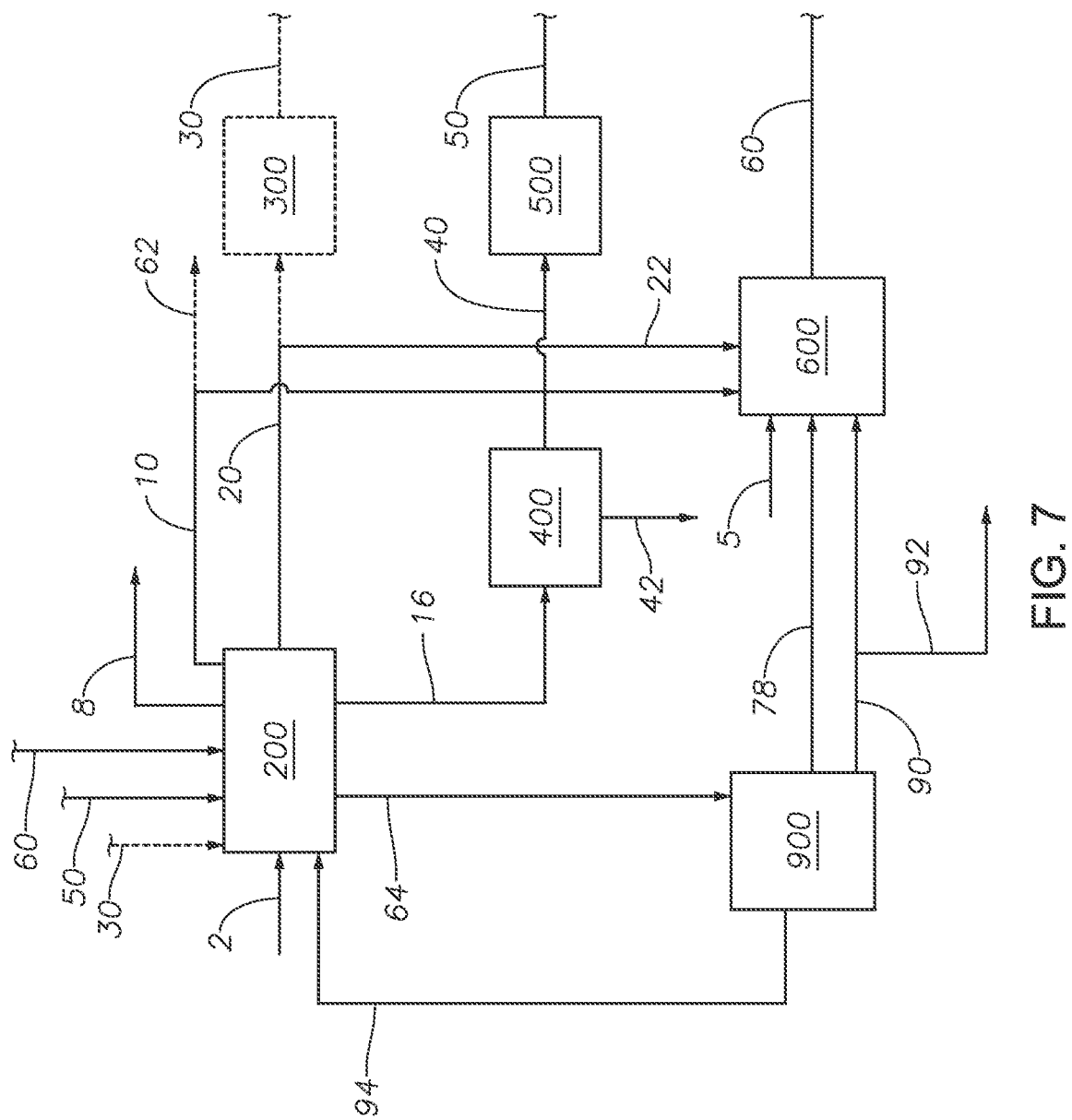
FIG. 7 provides a process diagram of the process for Example 4.

Example 4 is a comparative example. The process was simulated according to the process of FIG. 7. The process of FIG. 7 can be understood with reference to FIG. 6, where the process is in the absence of dealkylation reactor 100, such that no dealkylation occurs upstream of transalkylation reactor 600. Combined heavy stream 64 can flow directly into dealkylation splitter 900.

TABLE 4

Composition and flow rates for Example 4.

| | | 2 | 8 | 10 | 62 | 20 | 22 | 16 | 64 | 90 | 92 |
|---|---|---|---|---|---|---|---|---|---|---|---|
| Mass Flow | | 1598 | 122 | 126 | 63 | 702 | 695 | 5866 | 1800 | 22 | 101 |
| Hydrogen | kg/hr | 0 | 1 | 0 | 0 | 0 | 0 | 0 | 0 | 0 | 0 |
| Light Gas | kg/hr | 0 | 120 | 0 | 0 | 0 | 0 | 0 | 0 | 0 | 0 |
| Benzene | kg/hr | 49 | 0 | 126 | 63 | 0 | 0 | 0 | 0 | 0 | 0 |
| Toluene | kg/hr | 213 | 0 | 0 | 0 | 702 | 695 | 0 | 0 | 0 | 0 |
| p-xylene | kg/hr | 97 | 0 | 0 | 0 | 0 | 0 | 1320 | 0 | 0 | 0 |
| o-xylene & m-xylene | kg/hr | 291 | 0 | 0 | 0 | 0 | 0 | 4546 | 0 | 0 | 0 |
| MEB | kg/hr | 211 | 0 | 0 | 0 | 0 | 0 | 0 | 422 | 0 | 0 |
| TMB | kg/hr | 565 | 0 | 0 | 0 | 0 | 0 | 0 | 1131 | 0 | 0 |
| C10+ | kg/hr | 171 | 0 | 0 | 0 | 0 | 0 | 0 | 248 | 22 | 101 |

| | | 96 | 4 | 5 | 42 | 40 | 50 | 30 | 60 |
|---|---|---|---|---|---|---|---|---|---|
| Mass Flow | | 1578 | 8 | 8 | 1320 | 4546 | 4546 | 7 | 2466 |
| Hydrogen | kg/hr | 0 | 8 | 8 | 0 | 0 | 0 | 0 | 1 |
| Light Gas | kg/hr | 0 | 0 | 0 | 0 | 0 | 0 | 0 | 120 |
| Benzene | kg/hr | 0 | 0 | 0 | 0 | 0 | 0 | 3 | 74 |

TABLE 4-continued

Composition and flow rates for Example 4.

| | | | | | | | | | |
|---|---|---|---|---|---|---|---|---|---|
| Toluene | kg/hr | 0 | 0 | 0 | 0 | 0 | 0 | 0 | 489 |
| p-xylene | kg/hr | 0 | 0 | 0 | 1320 | 0 | 1046 | 1 | 177 |
| o-xylene & m-xylene | kg/hr | 0 | 0 | 0 | 0 | 4546 | 3500 | 3 | 752 |
| MEB | kg/hr | 422 | 0 | 0 | | 0 | 0 | 0 | 211 |
| TMB | kg/hr | 1131 | 0 | 0 | 0 | 0 | 0 | 0 | 565 |
| C10+ | kg/hr | 25 | 0 | 0 | 0 | 0 | 0 | 0 | 76 |

Comparing the results of Examples 3 and Example 4 shows that the addition of dealkylation reactor 100 reduces the flow rate of C9 aromatic hydrocarbons introduced to transalkylation reactor 600.

Although the embodiments have been described in detail, it should be understood that various changes, substitutions, and alterations can be made without departing from the principle and scope. Accordingly, the scope of the present embodiments should be determined by the following claims and their appropriate legal equivalents.

There various elements described can be used in combination with all other elements described here unless otherwise indicated.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed here as from about one particular value to about another particular value and are inclusive unless otherwise indicated. When such a range is expressed, it is to be understood that another embodiment is from the one particular value to the other particular value, along with all combinations within said range.

Throughout this application, where patents or publications are referenced, the disclosures of these references in their entireties are intended to be incorporated by reference into this application, in order to more fully describe the state of the art to which the invention pertains, except when these references contradict the statements made here.

As used here and in the appended claims, the words "comprise," "has," and "include" and all grammatical variations thereof are each intended to have an open, non-limiting meaning that does not exclude additional elements or steps.

That which is claimed is:

1. A system for producing para-xylene (p-xylene) from a reformate feed, the system comprising:
    a reformate splitter, the reformate splitter configured to separate the reformate feed, wherein the reformate feed comprises aromatic hydrocarbons, wherein the aromatic hydrocarbons are selected from the group consisting of benzene, toluene, mixed xylenes, carbon-nine plus (C9+) aromatic hydrocarbons, and combinations of the same, wherein the reformate splitter produces a light gases stream, a combined heavy stream, a benzene stream, a xylene stream, and a toluene stream, wherein the combined heavy stream comprises the C9+ aromatic hydrocarbons, and wherein the xylene stream comprises the mixed xylenes, wherein the mixed xylenes comprises p-xylenes;
    a dealkylation reactor fluidly connected to the reformate splitter, the dealkylation reactor configured to convert the C9+ aromatic hydrocarbons to carbon-six (C6) to carbon-eight (C8) aromatic hydrocarbons in the presence of a dealkylation catalyst to produce a dealkylation effluent, wherein the dealkylation reactor is at a dealkylation temperature, wherein the dealkylation reactor is at a dealkylation pressure, wherein the dealkylation effluent comprises aromatic hydrocarbons such that an amount of C9+ aromatic hydrocarbons in the dealkylation effluent is less than the amount of C9+ aromatic hydrocarbons in the reformate feed;
    a dealkylation splitter fluidly connected to the dealkylation reactor, the dealkylation splitter configured to separate the dealkylation effluent to produce a light recycle stream, a C10+ aromatics stream, and a C9 stream;
    a transalkylation reactor fluidly connected to the dealkylation reactor and fluidly connected to the reformate splitter, the transalkylation reactor configured to convert toluene and C9 aromatic hydrocarbons in the presence of a transalkylation catalyst to produce a transalkylation effluent, wherein the transalkylation reactor is at a transalkylation temperature, wherein the transalkylation reactor is at a transalkylation pressure, wherein the toluene is supplied by a toluene split stream, wherein the toluene split stream is separated from the toluene stream, wherein the transalkylation catalyst is operable to catalyze transalkylation reactions, wherein the transalkylation effluent comprises C6 to C9+ aromatic hydrocarbons;
    a p-xylene separation unit fluidly connected to the reformate splitter, the p-xylene separation unit configured to separate p-xylenes from the xylene stream to produce a p-xylene product and a p-xylene depleted stream, wherein the p-xylene product comprises p-xylenes, wherein the p-xylene depleted stream comprises meta-xylene (m-xylene) and ortho-xylene (o-xylene); and
    an isomerization unit fluidly connected to the p-xylene separation unit, wherein the isomerization unit is configured to convert the m-xylene and o-xylene in the p-xylene depleted stream to produce an isomerization effluent, wherein the isomerization unit is at an isomerization temperature, wherein the isomerization unit is at an isomerization pressure, wherein the isomerization effluent comprises C8 aromatic hydrocarbons.

2. The system of claim 1, wherein a volumetric flow rate of the toluene split stream is operable to maintain a volume ratio of toluene to trimethylbenzene in the transalkylation reactor in a range of 0.3 to 3.

3. The system of claim 1, wherein the dealkylation temperature is between 200° C. and 550° C., further wherein the dealkylation pressure is between 5 bar and 50 bar, and wherein a liquid hourly space velocity in the dealkylation reactor is between 1 hr$^{-1}$ and 20 hr$^{-1}$.

4. The system of claim 1, wherein the transalkylation temperature is between 200° C. and 550° C., further wherein the transalkylation pressure is between 10 bar and 50 bar, and wherein a liquid hourly space velocity in the transalkylation reactor is between 0.2 hr$^{-1}$ and 20 hr$^{-1}$.

5. The system of claim 1, wherein the isomerization temperature is between 200° C. and 550° C., further wherein the isomerization pressure is between 5 bar and 50 bar, and wherein a liquid hourly space velocity in the isomerization unit is between 1 hr$^{-1}$ and 20 hr$^{-1}$.

6. The system of claim 1, further comprising a toluene disproportionation reactor fluidly connected to the reformate splitter, the toluene disproportionation reactor configured to convert a fraction of the toluene from the toluene stream to produce a disproportionation effluent, wherein the disproportionation effluent comprises C6 to C8 aromatic hydrocarbons.

* * * * *